(12) United States Patent
Kodama

(10) Patent No.: US 6,937,889 B2
(45) Date of Patent: Aug. 30, 2005

(54) METHOD AND APPARATUS FOR DETERMINING PREGNANCY POSSIBILITY

(75) Inventor: Miyuki Kodama, Tokyo (JP)

(73) Assignee: Tanita Corporation, Tokyo (JP)

( * ) Notice: Subject to any disclaimer, the term of this patent is extended or adjusted under 35 U.S.C. 154(b) by 740 days.

(21) Appl. No.: 09/968,034

(22) Filed: Oct. 2, 2001

(65) Prior Publication Data

US 2002/0040194 A1 Apr. 4, 2002

(30) Foreign Application Priority Data

Oct. 2, 2000 (JP) .................................... 2000-302757

(51) Int. Cl.[7] .................................................. A61B 5/05
(52) U.S. Cl. ..................................... 600/547; 600/551
(58) Field of Search ................................. 600/300, 304, 600/547, 551, 587, 591

(56) References Cited

U.S. PATENT DOCUMENTS

| | | | |
|---|---|---|---|
| 4,685,471 A | * | 8/1987 | Regas et al. ................ 600/547 |
| 5,240,010 A | | 8/1993 | Weinmann |
| 6,110,125 A | | 8/2000 | Young et al. |
| 6,402,699 B1 | * | 6/2002 | Kodama et al. ............ 600/551 |

FOREIGN PATENT DOCUMENTS

| | | |
|---|---|---|
| DE | 198 52 559 | 5/2000 |
| EP | 0 498 303 | 8/1992 |
| EP | 1084676 | 3/2001 |
| JP | 2001-078977 | 3/2001 |

* cited by examiner

Primary Examiner—Max F. Hinderburg
Assistant Examiner—Jonathan Foreman
(74) Attorney, Agent, or Firm—McDermott Will & Emery LLP

(57) ABSTRACT

Disclosed are method and apparatus for making a decision of possibility of pregnancy in terms of how the values of bioelectrical impedance vary after expiration of a certain length of time since the ovulation day.

7 Claims, 6 Drawing Sheets

__US 6,937,889 B2__

METHOD AND APPARATUS FOR DETERMINING PREGNANCY POSSIBILITY

BACKGROUND OF THE INVENTION

1. Field of the Invention

The present invention relates to a method and apparatus for determining pregnancy possibility.

2. Prior Art

Women use clinical thermometers to measure their basal body temperature each and every day, and then they can make a decision of the possibility of being pregnant on the basis of the time-sequence transition or historical record of basal body temperatures. FIG. 1 shows the time-sequence transition or historical record of the basal body temperature of women who have a twenty eight day-long menstruation period. As shown, the physical phases of the monthly body condition the woman has are closely related with the time-sequence transition or historical record of the basal body temperature. The temperature curve (a) shows the normal body condition, transferring from the low-temperature period to the high-temperature period on the ovulation day, and conversely from the high-temperature period to the low-temperature period on the ovulation day. In case of anovulation the temperature curve (b) shows little or no noticeable variation, or no temperature transition as in the normal curve (a). In case of corpus luteum insufficiency the temperature curve (c) has its high-temperature period lasting ten or less days, much shorter than the normal curve (a). As may be understood from the above, the physical phases of the monthly body condition the woman has are reflected in the time-sequence transition or historical record of the basal body temperature. As shown in FIG. 2, the basal body temperature shows a noticeable change when the woman is pregnant. Specifically the basal body temperature rises on the ovulation day, and it remains at a high-temperature level until the beginning day of the menstruation period to lower gradually if the woman is not pregnant (see broken line on curve (a)) whereas the basal body temperature is remaining high for the menstruation period if the woman is pregnant (see solid line on curve (a)). A decision can be made on the pregnancy possibility on the basis of such graphs.

Another method of checking the pregnancy possibility uses test papers to detect hormone if any, in urine.

As for the decision-making of pregnancy possibility relying on basal body temperature it is required that a woman holding a clinical thermometer in her mouth is lying still a few minutes in bed. This is difficult to continue a long length of time, and women often fall in sleep in bed while measuring her basal body temperature.

As for the decision-making of pregnancy possibility relying on detection of hormone in urine it is not preferable from the hygienic point of view. Throwaway test paper cannot be repeatedly used, and is rather expensive.

SUMMARY OF THE INVENTION

In view of the above one object of the present invention is to provide a method of making a decision of the pregnancy-possibility with ease.

Another object of the present invention is to provide an apparatus of making a decision of the pregnancy-possibility with ease.

To attain these objects a pregnancy possibility determining method according to the present invention comprises the steps of: determining the value of bioelectrical impedance of a woman; presuming when the woman has the ovulation day from the so determined value of bioelectrical impedance and the time-sequence transition or historical record of the values of bioelectrical impedance, or by presuming the beginning day of next menstruation period from the time-sequence transition or historical record of the values of bioelectrical impedance and by counting a predetermined number of days backward from the so presumed beginning day of next menstruation period; and making a decision about the possibility of pregnancy in terms of whether or not a predetermined number of days has passed from the so presumed ovulation day with the values of bioelectrical impedance remaining low.

The possibility of pregnancy may be presumed when 21 days have passed from the ovulation day actually determined or from the presumed ovulation day with the values of bioelectrical impedance remaining low.

A pregnancy possibility determining apparatus according to the present invention comprises: a bioelectrical impedance meter; a bioelectrical impedance storing device; an ovulation decision-making unit or an ovulation presuming unit; a pregnancy decision-making unit; and a warning unit, wherein said bioelectrical impedance meter measures the value of bioelectrical impedance of a woman who is using the apparatus; said bioelectrical impedance storing device stores the so measured values of bioelectrical impedance; said ovulation decision-making unit makes a decision as to when the woman has the ovulation day on the basis of the time-sequence transition or historical record of the values of bioelectrical impedance stored in the bioelectrical impedance storing device; or said ovulation presuming unit counts a predetermined number of days from the beginning day of next menstruation period presumable from the time-sequence transition or historical record of the values of bioelectrical impedance stored in the bioelectrical impedance storing device, and said ovulation presuming unit presumes that the day so counted backward from the presumable beginning day of next menstruation period falls on the ovulation day; said pregnancy decision-making unit makes a decision of the possibility of pregnancy in terms of whether or not a predetermined number of days have passed from the ovulation day actually determined or presumed with the values of bioelectrical impedance remaining low; and said warning unit informs the woman of the result of decision-making of the possibility of pregnancy.

The pregnancy possibility determining apparatus may further comprise a physical condition decision-making unit, which can make a decision as to which physical phase of the monthly body condition the woman has presently on the basis of the time-sequence transition or historical record of the values of bioelectrical impedance stored in the bioelectrical impedance storing device, whereby the warning unit may inform the woman of which physical phase of the monthly body condition the woman has presently.

The possibility of pregnancy may be presumed when 21 days have passed from the ovulation day actually determined or from the presumed ovulation day with the values of bioelectrical impedance remaining low.

Pieces of information provided by the warning unit may be changed depending on how many days have passed from the ovulation day actually determined or from the presumed ovulation day with the values of bioelectrical impedance remaining low.

The possibility of pregnancy may be given by numerical value, and is provided by the warning unit, the numerical value depending on how many days have passed from the ovulation day actually determined or from the presumed ovulation day with the values of bioelectrical impedance remaining low.

The warning unit may inform the woman of the number of the days which have passed since the ovulation day actually determined or the presumed ovulation day.

The physical condition decision-making unit may make a decision as to whether the woman is supposed to be pregnant.

Other objects and advantages of the present invention will be understood from the following description of some preferred embodiment of the present invention, which are shown in accompanying drawings.

DESCRIPTION OF PREFERRED EMBODIMENTS

In a case where a woman ovulates to allow the ovum to be unfertilized for a certain length of time (usually fourteen days), the ovum which lack fertilizing capability will be released from her body (menstruation) and then her basal body temperature lowers. Even though she has no menstruation because of some disturbance of hormone her basal body temperature lowers. In a case where fertilized ovum is deposited, her basal body temperature does not lower, remaining at a high-value level for a long length of time. When the high-temperature period lasts 21 or more days, she is presumed to be pregnant.

Figure 1:
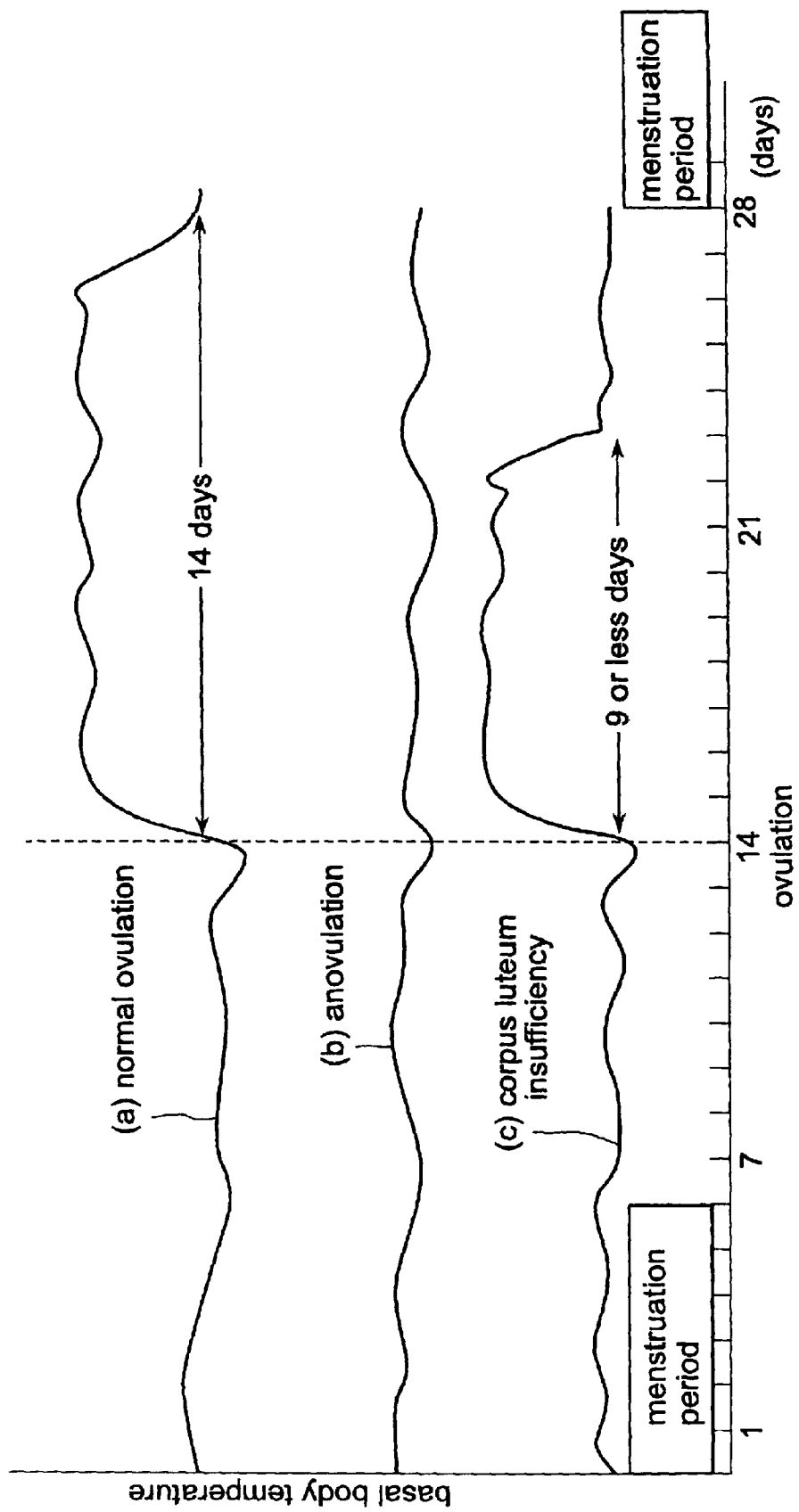
FIG. 1 is a graphic presentation showing how the basal body temperature of a selected woman varies.
Figure 2:
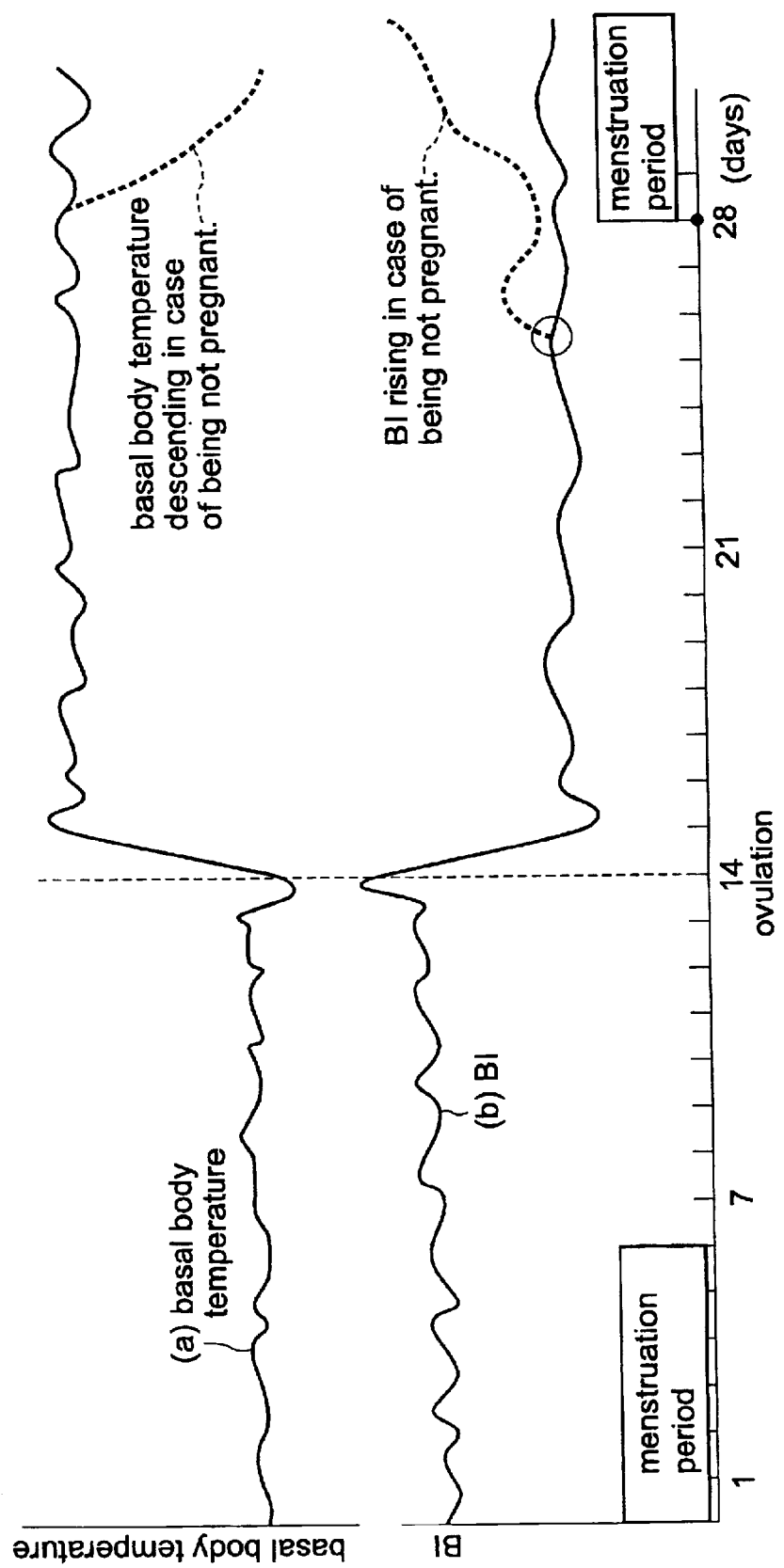
FIG. 2 is a graphic presentation showing how the basal body temperature and the value of bioelectrical impedance of the selected woman are related with the menstruation period.

The present applicant filed Patent Application No. H 11-258358, proposing that a decision be made as to which physical phases of the monthly body condition a woman has in terms of bioelectrical impedance. Specifically the value of bioelectrical impedance is closely related with the basal body temperature of the woman; it remains high while the basal body temperature remains low whereas it remains low while the basal body temperature remains high. As shown in FIG. 2(b), likewise the value of bioelectrical impedance shows a noticeable change when the woman is pregnant. Specifically the value of bioelectrical impedance lowers around the ovulation day, and the bioelectrical impedance continues to remain at a low value a few days earlier than the beginning day of the menstruation period, and then, it rises gradually if the woman is not pregnant (see broken line on curve (b) ) whereas the bioelectrical impedance curve remains low for the menstruation period if the woman is pregnant (see solid line on curve (b) ). The principle of the present invention uses this noticeable change indicating the pregnancy of the woman to make a decision of possible pregnancy in terms of whether the lowered value of bioelectrical impedance continues a certain length of time.

Figure 3:
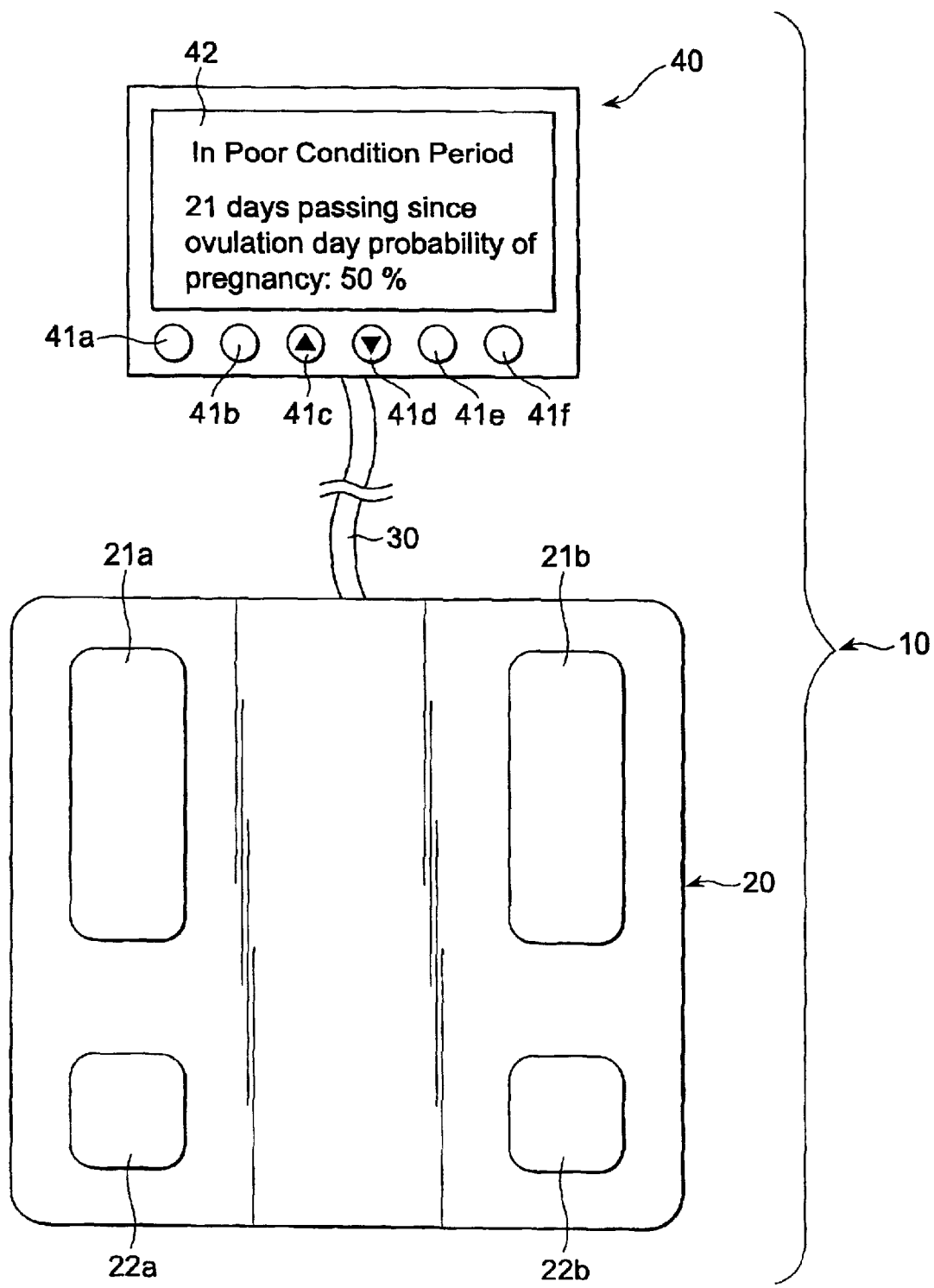
FIG. 3 illustrates a pregnancy possibility determining apparatus according to one preferred embodiment of the present invention in appearance.

Referring to FIG. 3, a pregnancy possibility determining apparatus according to one preferred embodiment of the present invention 10 comprises a scale-and-bioelectrical impedance meter 20 and a control box 40 connected to the scale-and-bioelectrical impedance via an electric cable 30 or via infrared or electromagnetic wave.

The scale-and-bioelectrical impedance meter 20 has constant current feeding electrodes 21a and 21b and voltage measuring electrodes 22a and 22b provided on its front side whereas the control box 40 has a set of operation buttons 41a to 41f and a display 42 provided on its front side. The set of operation buttons include a power source button 41a, a measurement button 41b, an UP digit-shifting button 41c, a DOWN digit-shifting button 41d, a "menstruation beginning day" inputting button 41e and a setting button 41f.

Figure 4:
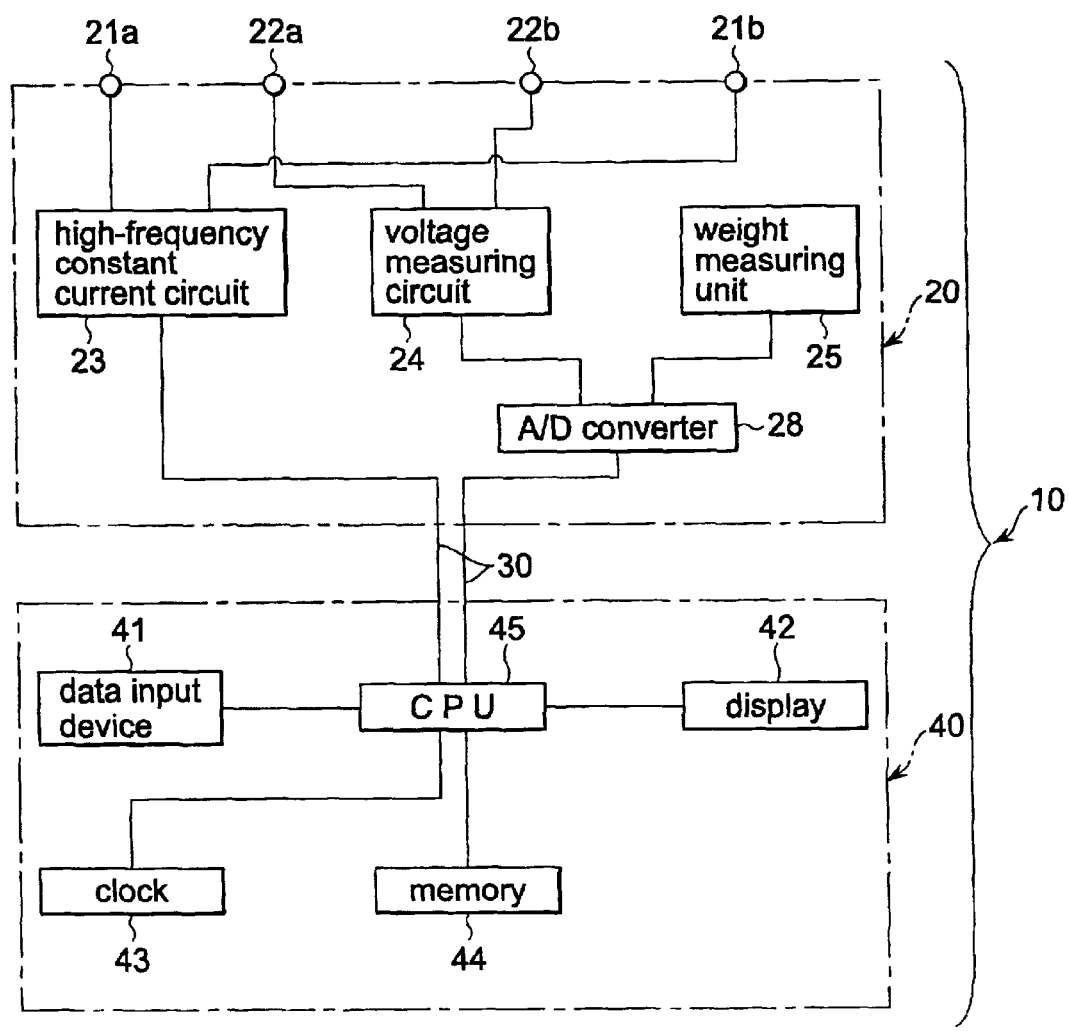
FIG. 4 is block diagram showing what functions make up the apparatus of FIG. 3.

FIG. 4 shows the functional structure of the pregnancy possibility determining apparatus 10. As shown in the drawing, the scale-and-bioelectrical impedance meter 20 comprises a high-frequency constant current circuit 23 for supplying a weak high-frequency current of fixed value to the constant current feeding electrodes 21a and 21b, a voltage measuring circuit 24 for measuring the voltage appearing between the voltage measuring electrodes 22a and 22b, a weight measuring unit 25, and an A/D converter 28 for converting the measured voltage and weight to digital values.

The control box 40 comprises a data input device 41 including a set of operation buttons 41a to 41f for inputting instructions for measurement, data pertaining to the menstruation period and other pieces of information, a display 42 for showing the time-sequence transition of measured bioelectrical impedance values, the possibility of pregnancy and such like, a clock 43 for determining the date and time on or at which the measurement is effected, a memory 44 for storing the measured bioelectrical impedance values, the measurement data, the physical phases the woman had on days previous to the present day and such like, and a CPU 45, which takes not only the arithmetic parts of: making a decision on the female physical condition and the possibility of pregnancy on the basis of data pertaining to the menstruation period inputted by the data input device 41, the measured bioelectrical impedance values and the weight of the woman; and selecting and storing data in the memory or selecting and showing data in the display 42, but also the part of presuming and making a decision on when the woman has an ovulation day, whether she is pregnant, and which physical phase of the monthly body condition she has.

In this particular embodiment the scale-and-bioelectrical impedance meter 20 and the control box 40 are separate, together making up the female physical condition managing apparatus. The CPU 45 may be installed in the scale-and-bioelectrical impedance meter 20. Otherwise, the scale-and-bioelectrical impedance meter 20 and the control box 40 may be combined as a whole.

Now, the manner in which the pregnancy possibility determining apparatus 10 works is described.

Figure 5:
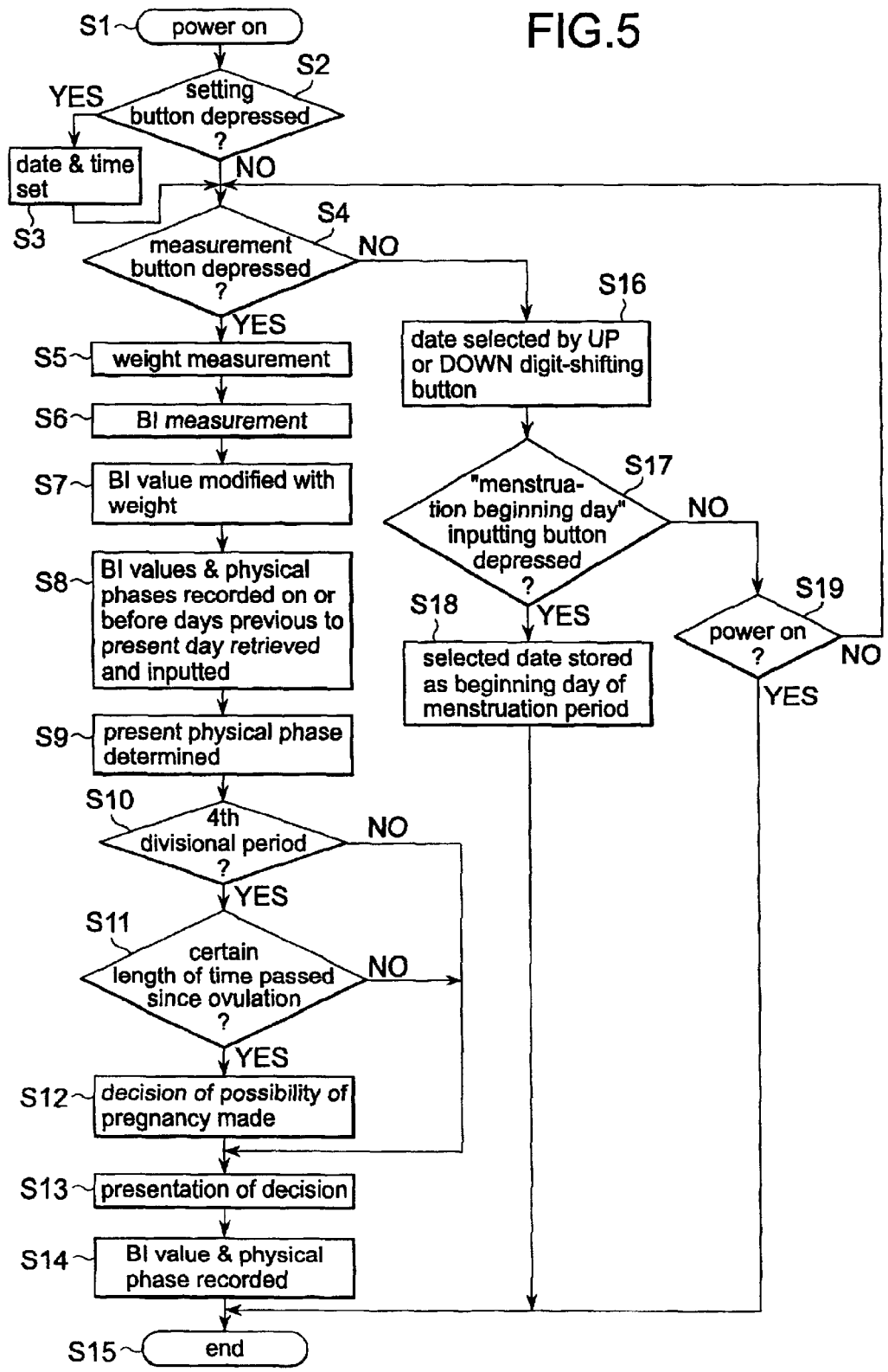
FIG. 5 is a flowchart showing the manner in which the apparatus of FIG. 3 works.

FIG. 5 is a flow chart showing the sequential steps to follow in making a decision on the monthly physical condition and the possibility of pregnancy of a woman who is using the apparatus 10. The woman depresses the power source switch 41a at STEP 1, thus putting the apparatus 10 in circuit with the power supply. Depression of the setting button 41f at STEP 2 puts the apparatus 10 in the setting mode, proceeding to Step 3 where the present date and time is set. Specifically the digits representing date and time are changed by using the UP digit-shifting button 41c and the DOWN digit-shifting button 41d until the present date and time appears in the display. Then, the present date and time is set by depressing the setting button 41f again. Likewise, the beginning day of the previous menstruation period is inputted and set.

Depression of the measurement button 41b at STEP 4 puts the apparatus 10 in the measurement mode, proceeding to STEP S5. If not, the apparatus is put in the menstruation data inputting mode, proceeding to STEP 16.

The measurement mode starts from STEP 5. The woman stands on her barefoot on the scale-and-bioelectrical impedance meter 20. Specifically she stands on the weight scale with the toes and heels of the left and right feet put on the constant current feeding electrodes 21a and 21b and the voltage measuring electrodes 22a and 22b respectively. Then, the measurement starts with the weight of the woman.

At STEP 6 the high-frequency constant current circuit 23 makes a high-frequency, weak current flow in her body via the constant current feeding electrode 21a, the toe of the left foot, the left leg, the lower part of her abdomen, the right leg, the toe of the right foot and the constant current feeding electrode 21b. The voltage measuring circuit 24 determines the voltage appearing between the voltage measuring electrodes 22a and 22b, thus determining the bioelectrical impedance value. At STEP 7 the bioelectrical impedance value is modified with weight according to the following equation 1 or 2:

bioelectrical impedance modified with weight=bioelectrical impedance+$A$×(difference of weight from the initial weight),     (1)

or bioelectrical impedance modified with weight=bioelectrical impedance+$B$×(difference of weight from the preceding weight),     (2)

where "A" and "B" stand for correction coefficients.

The so modified bioelectrical impedance value is independent from the influence caused by the varying weight.

At STEP 8 the bioelectrical impedance values measured on several days before the present day, the physical condition determined on the day before the present day, some data pertaining to the beginning day of the last menstruation period and other data are retrieved from the memory 44 to be put in the CPU 45.

At STEP 9 the CPU 45 makes, on the basis of the relation between the bioelectrical impedance values and the monthly body condition, a decision as to which physical phase or divisional period the woman is passing over, the first divisional period (the menstruation period), the second divisional period (the "in good condition" period), the third divisional period (the "not changing" period), the fourth divisional period (the "in poor condition" period) or the fifth divisional period (the pregnancy-possible period).

The following example of physical phases or divisional periods may fit women whose menstruation period lasts 28 days. It, however, should be noted that it depends on individuals how long each divisional period lasts.

Figure 6:
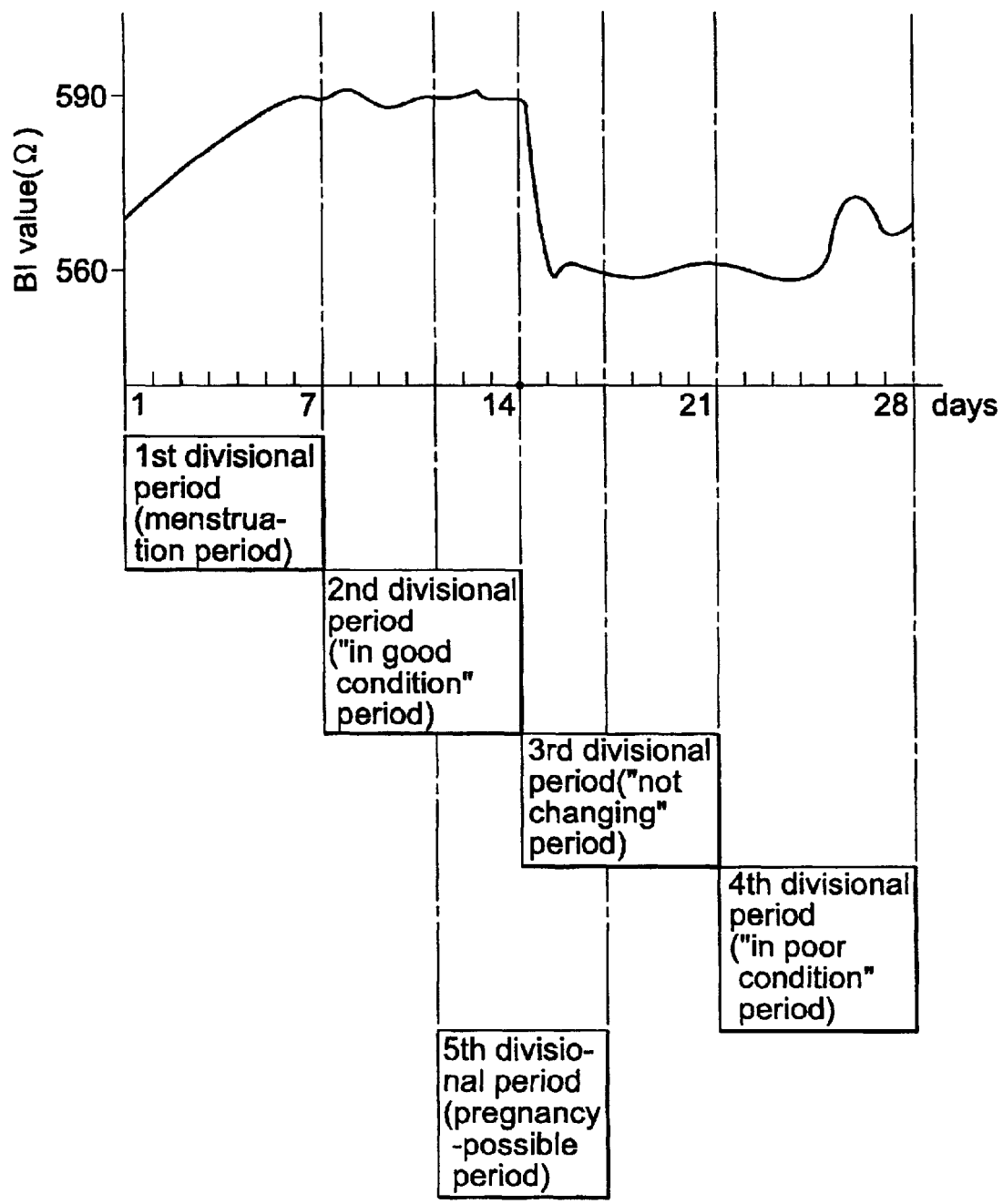
FIG. 6 is a graphic presentation showing which parts of the bioelectrical impedance represent which physical phases of the monthly body condition of the woman.

Referring to FIG. 6, the manner in which a decision is made on which divisional period the woman is passing over is described.

The seven days counted forward from the beginning day of the menstruation period are included in the "First Divisional Period" (the menstruation period). The "Second Divisional Period" (the "in Good Condition" Period) spans from the day following the termination of the "First Divisional Period" to the transient day on which the bioelectrical impedance transfers from the raised value to the lowered value. The seven days counted forward from the transient day make up the "Third Divisional Period" (the "not changing" period). The day subsequent to the termination of the "Third Divisional Period" to the beginning day of next menstruation period are included in the "Fourth Divisional Period" (the "in poor condition" period). Finally, the "Fifth Divisional Period" (the pregnancy-possible period) includes three days before and after the transient day on which the bioelectrical impedance transfers from the raised value to the lowered value. The transfer to the lowered value of bioelectrical impedance is determined by detecting the decrease of 4 or more percent with respect to the mean value of the raised values of bioelectrical impedance lasting some days just before the transient day.

As for the woman whose bioelectrical impedance values were plotted in FIG. 6 the mean value of raised bioelectrical impedance values is about 590 ohms, and the mean value of lowered bioelectrical impedance values is about 560 ohms. Accordingly the bioelectrical impedance curve is assumed to descend when detecting the bioelectrical impedance value of 566.4 or less ohms, which is 4% lower than 590 ohms. The lowered value of bioelectrical impedance was detected on the 15th day, and the pregnancy-possible period includes three days before and after the day.

The mean value of bioelectrical impedance values measured during the Fourth Divisional Period is about 560 ohms. When detecting that the bioelectrical impedance value is 554.4 ohms (one percent decrease) the degree of swelling is Level 1; when detecting that the bioelectrical impedance value is 544.8 ohms (two percent decrease) the degree of swelling is Level 2; when detecting that the bioelectrical impedance value is 543.2 ohms (three percent decrease) the degree of swelling is Level 3; and so forth.

In summary the month within which women have different physical phases is divided as follows:

the beginning day of the last menstruation period retrieved from the record and inputted is assumed to be the beginning day of the coming menstruation period;

the First Divisional Period (the menstruation period) starting from the beginning day of the menstruation period and lasting seven days;

the Second Divisional Period (the "in good condition" period) starting from the day subsequent to termination of the First Divisional Period to the day before the day on which four percent decrease is detected with respect to the mean value of the bioelectrical impedance values measured in the second period;

the Third Divisional Period (the "not changing" period) starting from the day subsequent to termination of the Second Divisional Period to the day one week earlier than the beginning day of next menstruation period presumed from the record; and the Fourth Divisional Period (the "in poor condition" period) starting from the day subsequent to termination of the Third Divisional Period and ending with the day on which the beginning day of the menstruation period is retrieved from the record and inputted next time.

The days are counted backward from the beginning day each of some selected menstruation periods to a selected ovulation day both retrieved from the record, and on the basis of the average number of the so counted days the ovulation day is presumed and determined. Then, the Fifth Divisional Period (the pregnancy possible period) is determined as containing three days before and after the so presumed ovulation day. In FIG. 6, the ovulation day happens to fall on the 14th day earlier than the presumed beginning day of next menstruation period. The ovulation day must be corrected at the time the transition from the raised bioelectrical impedance value to the lowered bioelectrical impedance value is actually detected. Specifically if the transition is detected to be earlier than the presumed ovulation day, the Fifth Divisional Period (the pregnancy-possible period) is determined as including the three days subsequent to the transition day thus confirmed. Conversely no transition is detected actually after the presumed ovulation day, and then the pregnancy-possible period is deemed to last three days from the actual ovulation day.

Thus, the woman using the apparatus 10 can realize which stage has been reached, and particularly that she may be supposed to be pregnant. A decision making is not permitted if the values of bioelectrical impedance measured during the last period are not available from the memory. In a case where no data is available no decision can be made.

At STEP 10 the CPU 45 starts the decision-making of the possibility of pregnancy. The possibility of pregnancy can be determined in terms of whether the value of bioelectrical impedance remaining low in the Fourth Divisional Period (the "in poor condition" period) rises a few days earlier than the beginning day of next menstruation period (see FIGS. 2 and 6). Assuming that at STEP 9 the CPU 45 has determined that the woman is being "in poor condition" in the Fourth Divisional Period, and that at STEP 16 the beginning day of the presumed next menstruation period is inputted as later described, the apparatus 10 continues the checking of the possibility of pregnancy, starting from the beginning of the Fourth Divisional Period (one week earlier than the beginning day of the presumed next menstruation period) to the day on which the woman inputs some data pertaining to the beginning day of next menstruation period actually confirmed.

Specifically in a case where the present physical condition of the woman is determined to be the one appearing in the Fourth Divisional Period (the "in poor condition" period) at STEP 10, a decision is made as to whether or not a certain length of time has passed since the last ovulation day. For example, the certain length of time is 18 days long. In the negative, or if 17 or less days have passed, it may be possible that the value of bioelectrical impedance remain still low for the reason of occasional high basal body temperature, and therefore, no decision making of possibility of pregnancy is permitted before expiration of the certain length of time.

After expiration of the certain length of time a decision of possibility of pregnancy is made in terms of how many days have passed since the ovulation day at STEP 12. The probability of pregnancy is given as for instance, follows: Probability Level of Pregnancy is "1" for 18 to 20 days passing; Probability Level of Pregnancy is "2" for 21 to 24 days passing; and Probability Level of Pregnancy is "3" for 25 or more days passing.

Otherwise, the probability of pregnancy may be given in percent as for instance, follows: Probability Level of Pregnancy is 20% for 18 days passing, subsequently allowing the increase of 10% each and every day; and Probability Level of Pregnancy is 50% when 21 days have passed, subsequently allowing the increase of 1% each and every day to the maximum of 60%.

At STEP 13 the display 42 shows the body condition and the possibility of pregnancy. Specifically the display 42 shows the woman's body condition appearing in each divisional period, as for instance, follows: the menstruation period in the First Divisional Period, the "in good condition" period in the Second Divisional Period, termination of the ovulation or the "not changing" period in the Third Divisional period, the PMS period or "in poor condition" period in the Fourth Period, and the pregnancy-possible period in the Fifth Divisional Period.

In a case where the woman is supposed to be pregnant (STEPs 10 to 12), the content to be displayed change with the Probability Level of Pregnancy as for instance follows: a warning message which reads "Some data show that you may be pregnant." appears in the display if Probability Level of Pregnancy is "1"; a warning message which reads "You are probably pregnant. How about having a test for pregnancy at hospital?" appears in the display if Probability Level of Pregnancy is "2"; and a warning message which reads "Data has been continuously indicating that you are pregnant. You'd better have a test for pregnancy at hospital." appears in the display if Probability Level of Pregnancy is "3".

In addition, the number of days passing since the ovulation day confirmed and the probability of pregnancy are shown as for instance, follows: "21 days have passed since the ovulation day, and the probability of pregnancy is 50%."

At STEP 14 the weight-modified bioelectrical impedance value measured this time, the present body condition, the date of measurement and some other data are stored in the memory 44. Then, at STEP 15 the power supply turns off automatically, and the measurement ends.

At STEP 16 the menstruation data inputting mode starts. A desired date is given in the display 42 by depressing the UP digit-shifting button 41c and the DOWN digit-shifting button 41d. At STEP 17 a decision is made as to whether or not the menstruation beginning day inputting button 41e was depressed. In the affirmative, the date selected at STEP 18 is stored in the memory 44 as the beginning day of the menstruation period. In the negative, at STEP 19 a decision is made as to whether or not the power source button 41a was depressed. In the affirmative, the power supply turns off at STEP 15, and the inputting of data is finished.

In the above described embodiment a decision of possibility of pregnancy is made in terms of whether the value of bioelectrical impedance remains 18 days since the ovulation day. The number of days passing since ovulation day may be changed. The numbers of days and the kinds of data given in the above described embodiment may be changed as required.

The ovulation day is supposed to fall on the day on which the value of bioelectrical impedance transfers from the high-level period to the low level period. Otherwise, the ovulation day can be determined in the same way as the Fifth Divisional Period (the pregnancy-possible period). Specifically the average number of days counted from the beginning day of the menstruation period to the ovulation day is determined from the historical record, and the ovulation day can be determined statistically by counting the so determined average number of days backward from the beginning day of next menstruation period, which is presumed from the historical record. A decision of the possibility of pregnancy can be made in terms of how many days have passed since the so presumed ovulation day.

The probability of pregnancy described above should not be understood to be limitative. Appropriate modifications are possible to represent different degrees of probability.

Likewise, divisional periods characteristic of different physical phases of the monthly body condition can be given in different ways other than those described above, and some divisional periods may be partly overlapped.

The display is described above as warning means. Pieces of information may be given in the form of pictures or graphs or figures. Another practice of presenting pieces of information is a menu collecting pieces of information and lamps each allotted to each piece of information in the menu. When one piece of information is selected, the associated lamp turns on. Pieces of information pertaining to the possibility of pregnancy may be given orally.

In the above described embodiment the value of bioelectrical impedance is described as being modified with weight, and a decision of the physical phase and the possibility of pregnancy is made in terms of how the weight-modified value of bioelectrical impedance changes with time. It, however, may suffice that the value of bioelectrical impedance be used without being modified with weight. In the above described embodiment the value of bioelectrical impedance appearing between both feet of the woman is measured, but that appearing between both hands or between one hand and one foot of the woman can be equally used.

As may be understood from the above, the method and apparatus for making a decision of possibility of pregnancy according to the present invention permits a woman to make a quick decision as to whether or not she is pregnant on the basis of the variation of bioelectrical impedance values without burdening on her body. She does not bother to measure her basal body temperature while lying in bed every morning.

The present apparatus permits her to realize which physical phase of the monthly body condition she has presently, thereby releasing her from anxieties, which otherwise, she would have by getting a wrong idea of unpleasing physical condition.

What is claimed is:

1. A pregnancy possibility determining apparatus comprising:

a plurality of pairs of electrodes; a bioelectrical impedance meter; a bioelectrical impedance storing device; an ovulation decision-making unit or an ovulation presuming unit; a pregnancy decision-making unit; and a warning unit, wherein said pairs of electrodes can be applied to selected points of the outer layer of the skin of a woman's body;

said bioelectrical impedance meter measures the value of the bioelectrical impedance appearing between one of said pairs of electrodes;

said boielectrical impedance storing device stores the so measured values of bioelectrical impedance;

said ovulation decision-making unit makes a decision as to when the woman has an ovulation day on the basis of a time-sequence transition or historical record of the values of bioelectrical impedance stored in the bioelectrical impedance storing device; or said ovulation presuming unit counts a predetermined number of days from the beginning of a next menstration period presumable from the time-sequence transition or historical record of the values of bioelectrical impedance stored in the bioelectrical impedance storing device, and said ovulation presuming unit presumes that the day so counted backward from the presumable beginning day of the next menstration period falls on the ovulation day;

said pregnancy decision-making unit makes a decision of the possibility of pregnancy in terms of whether or not a predetermined number of days have passed from the ovulation day actually determined or presumed with the values of bioelectrical impedance remaining low; and said warning unit informs the woman of the result decision-making of the possibility of pregnancy.

2. A pregnancy possibility determining apparatus according to claim 1 wherein it further comprises a physical condition decision-making unit, which can make a decision as to which physical phase of the monthly body condition the woman has presently on the basis of the time-sequence transition or historical record of the values of bioelectrical impedance stored in the bioelectrical impedance storing device, whereby the warning unit may inform the woman of which physical phase of the monthly body condition the woman has presently.

3. A pregnancy possibility determining apparatus according to claim 1 or 2 wherein the possibility of pregnancy is presumed when 21 days have passed from the ovulation day actually determined or from the presumed ovulation day with the values of bioelectrical impedance remaining low.

4. A pregnancy possibility determining apparatus according to claim 1 or 2 wherein pieces of information provided by the warning unit are changed depending on how many days have passed from the ovulation day actually determined or from the presumed ovulation day with the values of bioelectrical impedance remaining low.

5. A pregnancy possibility determining apparatus according to claim 1 or 2 wherein the possibility of pregnancy is given by numerical value, and is provided by the warning unit, the numerical value depending on how many days have passed from the ovulation day actually determined or from the presumed ovulation day with the values of bioelectrical impedance remaining low.

6. A pregnancy possibility determining apparatus according to claim 1 or 2 wherein the warning unit informs the woman of the number of the days which have passed since the ovulation day actually determined or the presumed ovulation day.

7. A pregnancy possibility determining apparatus according to claim 2 wherein the physical condition decision-making unit makes a decision as to whether the woman is supposed to be pregnant.

* * * * *